United States Patent [19]

Bronstert et al.

[11] Patent Number: 4,822,945
[45] Date of Patent: Apr. 18, 1989

[54] PREPARATION OF DECENE OLIGOMERS AND USE THEREOF AS LUBRICATING OILS

[75] Inventors: Klaus Bronstert, Carlsberg; Helmut Mach, Heidelberg; Hans P. Rath, Gruenstadt; Hans-Michael Walter, Ruppertsberg, all of Fed. Rep. of Germany

[73] Assignee: BASF Aktiengesellschaft, Ludwigshafen, Fed. Rep. of Germany

[21] Appl. No.: 128,342

[22] Filed: Dec. 3, 1987

[30] Foreign Application Priority Data

Dec. 3, 1986 [DE] Fed. Rep. of Germany ....... 3641237

[51] Int. Cl.$^4$ .............................................. C07C 2/02
[52] U.S. Cl. ..................... 585/517; 585/520; 585/521; 585/522; 585/532
[58] Field of Search ............... 585/517, 520, 521, 522, 585/532

[56] References Cited

U.S. PATENT DOCUMENTS

| | | | |
|---|---|---|---|
| 3,637,503 | 1/1972 | Giannetti et al. | 260/683.15 |
| 3,725,498 | 4/1973 | Brennan | 252/59 |
| 4,041,098 | 8/1977 | Loveless | 585/521 |
| 4,533,782 | 8/1985 | Merijanian | 585/520 |

*Primary Examiner*—Curtis R. Davis
*Attorney, Agent, or Firm*—Keil & Weinkauf

[57] ABSTRACT

Decene oligomers useful with or without hydrogenation as basis for synthetic lubricating oils are prepared by oligomerizing decene-1 in the presence of an alkylaluminum chloride catalyst and an alkyl halide cocatalyst, in a first reaction stage the decene-1 being mixed with the catalyst at from 0 to +25° C. and being kept in contact therewith within the same temperature range for not less than 15 minutes and in a second reaction stage the cocatalyst being added at from 0 to +35° C. in the course of a period of from 15 to 180 minutes.

7 Claims, No Drawings

PREPARATION OF DECENE OLIGOMERS AND USE THEREOF AS LUBRICATING OILS

The present invention relates to a process for preparing a decene oligomer by oligomerizing decene-1 in the presence of an alkylaluminum chloride catalyst and an alkyl halide cocatalyst at low temperatures by stirring in the absence of air and water in a reactor.

Processes of this type produce decene oligomers which are useful as synthetic lubricating oils.

However, existing catalysts for preparing decene oligomers have certain disadvantages, for example poor solubility, low decene conversion, low degree of oligomerization or the need to premix catalyst and cocatalyst in a solvent.

It is known from U.S. Pats. Nos. 3,637,503 and 3,725,498 to use aluminum halide catalysts in combination with cocatalysts (for example HCl, carboxylic esters) for the oligomerization of olefins. However, these catalysts are of limited solubility and impair reproducibility. U.S. Pat. No. 3,382,291 likewise describe BF$_3$/cocatalyst combinations, suitable cocatalysts being water, alcohol, ethers and other organic compounds. BF$_3$, however, produces mainly low degrees of oligomerization and hence low reaction product viscosities.

U.S. Pat. No. 4,533,782 describes a process wherein a catalyst/cocatalyst solution comprising (a) an aluminum halide or organoaluminum compound, (b) an alkyl halide and (c) a solvent is premixed. The disadvantage with this existing process is the need to premix the catalyst solution and to separate the solvent from the reaction product.

It is an object of the present invention to avoid the disadvantages described above and to provide a technically simple process for substantially complete oligomerization of decene-1.

We have found that this object is achieved by a process as claimed in claim 1 or 2 or 3 or 4 or 5 or 6 or 7.

The customary processes for preparing decene oligomers by means of catalyst/cocatalyst combinations of the type described at the beginning are so well known, for example from the references cited above, as to require no further explanation. In the prior art, ethylaluminum dichloride is preferred as a particularly suitable alkylaluminum halide, and the alkyl halide used is preferably tert. -butyl chloride. An oligomer is a polymerization product which consists of few monomers, ie. has a low degree of polymerization. Preferably, the decene oligomers have a kinematic viscosity of from 3 to 200 mm$^2$/s at 100° C., as determined in accordance with German Standrad Specification DIN 51,562.

It has been found then, surprisingly, that, using an alkylaluminum halide as catalyst and an alkyl halide as cocatalyst, two-stage mixing of decene-1 with said alkylaluminum halide and subsequently with said alkyl halide produces a homogeneous reaction system giving complete decene-1 conversion, so that no decene-1 need be recycled.

In the process of the invention for preparing a decene oligomer by oligomerizing decene-1 in the presence of an alkylaluminum chloride catalyst and alkyl halide cocatalyst by stirring in the absence of air and water in a reactor, in a first reaction stage the decene-1 is mixed with the catalyst at from 0° to +25° C., preferably from 5 to +15° C., and kept in contact therewith within the same temperature range for not less than 15 minutes, preferably for from 30 to 120 minutes, and in a second reaction stage the cocatalyst is added at from 0° to +35° C., preferably from +5° to 30° C., in the course of a period of from 15 to 180, preferably from 15 to 60, minutes.

In the process according to the invention, the cocatalyst is added a little at a time or continuously.

The heat of reaction is removed from the oligomerization proces by external cooling, so that the temperature of the reaction mixture does not exceed +35° C. The molar ratio of catalyst:cocatalyst is within the range from 1:0.5 to 1:5.0, and the amount of catalyst, based on decene-1, is in the range from 0.1 to 5.0 percent by weight.

Alkylaluminum halides have the general formula R$_n$ALX$_{3-n}$, where R is alkyl, eg. methyl, ethyl, butyl and the like, and X is chlorine or bromine; n can be 1 or 2. Alkyl halides have the general formula R'X, where R' is alkyl, eg. ethyl, propyl, n-butyl and the like, and X is chlorine or bromine. A preferred combinatioon is ethylaluminum dichloride with tert. -butyl chloride.

The alkylaluminum halide may be used in solution in decene-1 or in decene oligomers.

As is customary with organometallic compounds, all the starting materials and apparatus must be free of water and/or air and other reactive materials. To this end, the decene-1 can be dried, for example, over a molecular sieve, and the stirred reactor be inertized by heating and flushing with dry nitrogen.

The reaction batch is worked up in a conventional manner by removing catalyst residues by washing with water or dilute hydrochloric acid.

The decene conversion can be determined for example by fractional distillation or gel permeation chromatography (GPC). A suitable GPC system comprises a 25 cm $^R$Lichrogel column PS4 (Merck, Darmstadt), on which the reaction mixture is separated using tetrahydrofuran as eluent at a flow rate or 1 ml/min. Detection can be for example by a refractive index detector.

In synthetic lubricating oils, the use of a wholly saturated material is desirable. To this end, the reaction mixture can be hydrogenated to avoid the presence of any unsaturation. Processes for producing synthetic lubricants based on decene oligomers are described in U.S. Pat. No. 3,149,178.

The Example which follows merely serves to illustrate the invention without limiting it.

EXAMPLE 100 g of decene-1 (0.71 mol) were introduced into a 250 ml four-necked flask in a nitrogen atmosphere and cooled down to +7° C. While stirring, 7.87 mmol of EtAlCl$_2$ (1.11 mol % or 1.00 % by weight of EtAlCl$_2$, based on decene-1) were added by means of a glass syringe through a neck of the reaction flask sealed with a rubber septum stopper. Without exotherm, stirring was continued at from +7° to +8° C. for 90 min. 0.87 ml of tert. -butyl chloride (0.73 g=7.87 mmol) was then added in 0.1 ml portions in the course of 25 min, each portion causing the temperature to rise (maximum temperature 26° C.). Thereafter, stirring was continued for a further 65 min, during which the temperature dropped to +7° C.

Samples were taken for GPC at 90, 120 and 180 min. GPC revealed the following composition in area %:

| Reaction time (min) | Decene-1 (area %) | Oligomers (area %) |
|---|---|---|
| 90 | 35.31 | 64.69 |
| 120 | — | 100.00 |
| 180 | — | 100.00 |

The reference product was worked up by repeated washing with water and drying over MgSO$_4$. According to GPC and distillative determination, the decene-1 conversion was quantitative. The kinematic viscosity was 20 mm$^2$/s at 100° C., determined in accordance with German Standard Specification DIN 51,562.

We claim:

1. A process for the substantially complete oligomerization of decene-1 which comprises:

mixing decene-1 with an alkylaluminum chloride catalyst in a reactor in a first reaction stage in the absence of air and water at a temperature of from 0° to +25° C. and over a period of not less than 15 minutes, said mixing of decene-1 and catalyst taking place in the absence of alkyl halide cocatalyst; and adding alkyl halide cocatalyst in a second reaction stage to the first stage reaction mixture at a temperature of from 0° to +35° C. over a period of 15 to 180 minutes.

2. The process of claim 1, wherein the temperature in the first reaction stage is maintained at from 5° to +15° C.

3. The process of claim 1, wherein the decene-1 is kept in contact with the catalyst for from 30 to 120 minutes.

4. The process of claim 1, wherein the cocatalyst is added a little at a time.

5. The process of claim 1, wherein the cocatalyst is added continuously.

6. The process of claim 1, wherein the temperature in the second reaction stage is maintained at from 5° to 30° C.

7. The process of claim 1, wherein the period over which the cocatalyst is added in the second reaction stage ranges from 15 to 60 minutes.

* * * * *